United States Patent
Kiguchi

(10) Patent No.: US 10,485,233 B2
(45) Date of Patent: Nov. 26, 2019

(54) METHOD FOR INCREASING YIELD OF CROP SEEDS OR FRUITS IN NUMBER OR WEIGHT

(71) Applicant: Sumitomo Chemical Company, Limited, Tokyo (JP)

(72) Inventor: So Kiguchi, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 480 days.

(21) Appl. No.: 14/651,035

(22) PCT Filed: Dec. 13, 2013

(86) PCT No.: PCT/JP2013/084172
§ 371 (c)(1),
(2) Date: Jun. 10, 2015

(87) PCT Pub. No.: WO2014/098201
PCT Pub. Date: Jun. 26, 2014

(65) Prior Publication Data
US 2015/0313218 A1   Nov. 5, 2015

(30) Foreign Application Priority Data
Dec. 21, 2012   (JP) .................. 2012-279043

(51) Int. Cl.
| A01N 43/653 | (2006.01) |
|---|---|
| A01N 33/08 | (2006.01) |
| A01N 37/18 | (2006.01) |
| A01N 37/38 | (2006.01) |

(52) U.S. Cl.
CPC ............ *A01N 37/18* (2013.01); *A01N 37/38* (2013.01); *A01N 43/653* (2013.01)

(58) Field of Classification Search
CPC .............................. A01N 43/653; A01N 33/08
See application file for complete search history.

(56) References Cited

U.S. PATENT DOCUMENTS

| 5,948,819 | A | 9/1999 | Ohtsuka et al. | |
|---|---|---|---|---|
| 6,313,150 | B1 | 11/2001 | Ohtsuka et al. | |
| 2007/0093389 | A1* | 4/2007 | Rademacher | A01N 37/50 504/116.1 |
| 2008/0293798 | A1 | 11/2008 | Dietz et al. | |
| 2009/0305893 | A1 | 12/2009 | Mills et al. | |
| 2010/0029479 | A1* | 2/2010 | Nowakowski | A01N 43/36 504/100 |
| 2011/0105331 | A1 | 5/2011 | Ebbinghaus et al. | |
| 2011/0196000 | A1 | 8/2011 | Ebbinghaus et al. | |
| 2011/0269623 | A1 | 11/2011 | Takaishi et al. | |
| 2012/0046323 | A1 | 2/2012 | Fought et al. | |
| 2012/0122677 | A1 | 5/2012 | Kurahashi | |
| 2012/0329799 | A1 | 12/2012 | Kiguchi et al. | |
| 2013/0012552 | A1 | 1/2013 | Kiguchi et al. | |
| 2013/0324413 | A1 | 12/2013 | Matsushima et al. | |

FOREIGN PATENT DOCUMENTS

| JP | 5041501 | B2 | 10/2012 |
|---|---|---|---|
| WO | 0210101 | A1 | 2/2002 |
| WO | 2007068421 | A2 | 6/2007 |
| WO | 2010137673 | A1 | 12/2010 |
| WO | 2011108123 | A2 | 9/2011 |
| WO | 2011108751 | A2 | 9/2011 |
| WO | 2011108760 | A2 | 9/2011 |
| WO | WO2011-108123 | * | 9/2011 |
| WO | 2012013590 | A2 | 2/2012 |
| WO | 2012133907 | A1 | 10/2012 |

OTHER PUBLICATIONS

Office Action dated Aug. 18, 2016 in CN Application No. 201380066096.5.
Examination Report dated Sep. 15, 2016 in AU Application No. 2013364884.
Supplemental Search Report dated Aug. 23, 2016 in EP Application No. 13864993.
Search Opinion dated Aug. 23, 2016 in EP Application No. 13864993.4.
Int'l Search Report dated Feb. 18, 2014 in Int'l Application No. PCT/JP2013/084172.
Examination Report dated Jan. 5, 2017 in AU Application No. 2013364884.
Examination Report dated Mar. 20, 2017 in AU Application No. 2013364884.
MacKenzie et al., "Uniformity of Strawberry Yield and Incidence of Botrytis Fruit Rot in an Annual Production System", Plant Disease, vol. 87, pp. 991-998 (Aug. 2003).
Office Action dated May 29, 2017 in EP Application No. 13864993.4.
Summons to Attend Oral Proceedings issued Dec. 5, 2017 in EP Application No. 13864993.4.
Office Action dated Feb. 1, 2016 in CN Application No. 201380066096.5.

\* cited by examiner

*Primary Examiner* — Rachael E Bredefeld
*Assistant Examiner* — Chris E Simmons
(74) *Attorney, Agent, or Firm* — Panitch Schwarze Belisario & Nadel LLP

(57) ABSTRACT

A method is provided for increasing the number or weight of seeds or fruits of a crop, including a step of treating the crop with effective amounts of a compound represented by Formula (1) and at least one compound selected from the group (A):

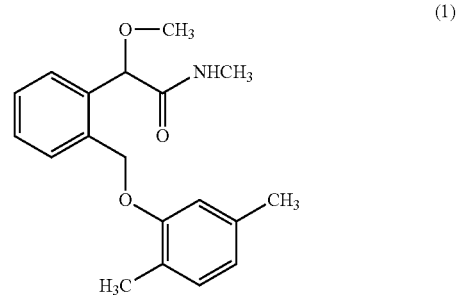

(1)

Group (A): tebuconazole, prothioconazole, cyproconazole, metconazole, boscalid, fluopyram, fluxapyroxad, azoxystrobin, dimoxystrobin, pyraclostrobin, trifloxystrobin, and picoxystrobin.

4 Claims, No Drawings

METHOD FOR INCREASING YIELD OF CROP SEEDS OR FRUITS IN NUMBER OR WEIGHT

CROSS-REFERENCE TO RELATED APPLICATION

This application is a Section 371 of International Application No. PCT/JP2013/084172, filed Dec. 13, 2013, which was published in the Japanese language on Jun. 26, 2014, under International Publication No. WO 2014/098201 A1, and the disclosure of which is incorporated herein by reference.

TECHNICAL FIELD

The present invention relates to a method for increasing the number or weight of seeds or fruits of a crop.

BACKGROUND ART

As fungicides, α-substituted phenylacetic acid compounds (see e.g. Patent Document 1) and other compounds (see e.g. Non-Patent Document 1 and Patent Document 2) are conventionally known. Meanwhile, a method for increasing yields of crop seeds or fruits in number or weight has always been demanded.

PRIOR ART DOCUMENTS

Patent Documents

Patent Document 1: WO 95/27693 A
Patent Document 2: WO 2007/017416 A

Non-Patent Document

Non-Patent Document 1: "The Pesticide Manual—15th edition (published by BCPC) ISBN 978-1-901396-18-8"

SUMMARY OF THE INVENTION

Problems to be Solved by the Invention

An object of the present invention is to provide a method for increasing the number or weight of seeds or fruits of a crop.

Means for Solving the Problems

The present inventors found a method for increasing the number or weight of seeds or fruits of a crop by treating a crop with a compound represented by Formula (1) and at least one compound selected from the group (A).

That is, the present invention is as follows.

[1] A method for increasing the number or weight of seeds or fruits of a crop, the method comprising a step of treating a crop with effective amounts of a compound represented by Formula (1) and at least one compound selected from the group (A);

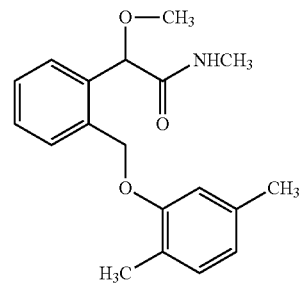

Group (A): a group consisting of tebuconazole, prothioconazole, cyproconazole, metconazole, boscalid, fluopyram, fluxapyroxad, azoxystrobin, dimoxystrobin, pyraclostrobin, trifloxystrobin and picoxystrobin.

[2] The method according to [1], wherein the at least one compound selected from the group (A) is tebuconazole, prothioconazole, cyproconazole or metconazole.

[3] The method according to [1], wherein the at least one compound selected from the group (A) is boscalid, fluopyram or fluxapyroxad.

[4] The method according to [1], wherein the at least one compound selected from the group (A) is azoxystrobin, dimoxystrobin, pyraclostrobin, trifloxystrobin or picoxystrobin.

[5] The method according to any one of [1] to [4], wherein the weight ratio of the compound represented by Formula (1) to the at least one compound selected from the group (A) is the compound represented by Formula (1)/the compound(s) selected from the group (A)=from 0.0125/1 to 500/1.

[6] The method according to any one of [1] to [5], wherein the compound represented by Formula (1) has R-absolute configuration.

[7] The method according to any one of [1] to [6], wherein the crop is rapeseed, rice, corn, wheat, barley, kidney bean, soybean, peach, apple or common pear.

[8] Use of a compound represented by Formula (1) and at least one compound selected from the group (A), the use as an agent to increase the number or weight of seeds or fruits of a crop;

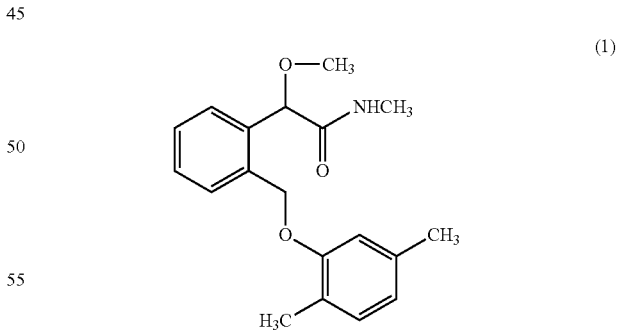

Group (A): a group consisting of tebuconazole, prothioconazole, cyproconazole, metconazole, boscalid, fluopyram, fluxapyroxad, azoxystrobin, dimoxystrobin, pyraclostrobin, trifloxystrobin and picoxystrobin.

MODE FOR CARRYING OUT THE INVENTION

The increase method involved in the present invention (hereinafter, can be referred to as "the present method") is a method for treating a crop with effective amounts of a compound represented by Formula (1) (hereinafter, can be referred to as "Compound (1)") and at least one compound selected from the group (A) (hereinafter, can be referred to as "Compound (A)");

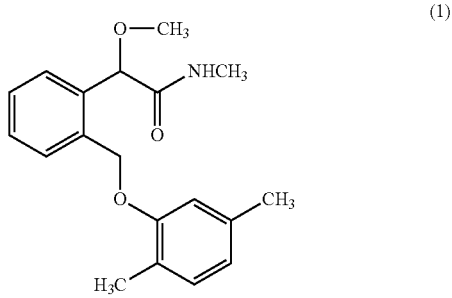

(1)

Group (A): a group consisting of tebuconazole, prothioconazole, cyproconazole, metconazole, boscalid, fluopyram, fluxapyroxad, azoxystrobin, dimoxystrobin, pyraclostrobin, trifloxystrobin and picoxystrobin.

Compound (1) is a known compound and can be produced by methods described in, for example, WO 95/27693 A pamphlet and WO 02/10101 A, and the like.

Tebuconazole, prothioconazole, cyproconazole, metconazole, boscalid, fluopyram, azoxystrobin, dimoxystrobin, pyraclostrobin, trifloxystrobin and picoxystrobin are all known compounds and, for example, described on pages 1072, 965, 287, 749, 121, 535, 62, 383, 971, 1167 and 910 of "The Pesticide Manual Fifteenth edition" published by British Crop Protection Council (BCPC). Fluxapyroxad is described in WO 2007/017416 A. These compounds can be obtained from commercial formulations or can be produced by known methods.

Compound (1) has an asymmetric carbon atom, and those which have any enantiomeric ratio can be used as Compound (1) in the present method. In terms of activity, Compound (1) with an R absolute configuration is preferably used.

In the present method, the weight ratio of Compound (1) to Compound (A) is usually Compound (1)/Compound (A)=0.0125/1 to 500/1, preferably 0.025/1 to 100/1, and more preferably 0.1/1 to 10/1.

In the present method, (although Compound (1) and Compound (A) can be each individually used) it is preferred that mixtures obtained by simply mixing Compound (1) and Compound (A) be used, and it is more preferred that formulations, such as oil solutions, emulsifiable concentrates, flowables, wettable powders, water dispersible granules, dusts and granules, obtained by mixing Compound (1), Compound (A) and an inert carrier, and adding a surfactant and other auxiliaries for formulations as necessary, be used.

In the present method, the total amount of Compound (1) and Compound (A) is usually 0.1 to 99% by weight, preferably 0.2 to 90% by weight and more preferably 1 to 80% by weight.

Examples of solid carriers used when producing formulations include fine powders or granules comprising, for example, minerals such as kaolin clay, attapulgite clay, bentonite, montmorillonite, acid clay, pyrophyllite, talc, diatomaceous earth and calcite, natural organic substances such as corn cob powders and walnut shell powders, synthetic organic substances such as urea, salts such as calcium carbonate and ammonium sulfate, and synthetic inorganic substances such as synthetic hydrated silicon oxide, and the like. Examples of liquid carriers include aromatic hydrocarbons such as xylene, alkylbenzene and methylnaphthalene, alcohols such as 2-propanol, ethylene glycol, propylene glycol and ethylene glycol monoethyl ether, ketones such as acetone, cyclohexanone and isophorone, vegetable oils such as soybean oil and cottonseed oil, petroleum aliphatic hydrocarbons, esters, dimethyl sulfoxide, acetonitrile and water.

Examples of the surfactant include anionic surfactants such as alkylsulfuric acid ester salts, alkylarylsulfonic acid salts, dialkylsulfosuccinic acid salts, polyoxyethylene alkyl aryl ether phosphoric acid ester salts, lignin sulfonic acid salts and naphthalene sulfonate formaldehyde polycondensates, and nonionic surfactants such as polyoxyethylene alkyl aryl ethers, polyoxyethylene alkylpolyoxypropylene block copolymers and sorbitan fatty acid esters, and cationic surfactants such as alkyltrimethylammonium salts.

Examples of the other auxiliaries for formulations include water-soluble polymers such as polyvinyl alcohols and polyvinylpyrrolidones, polysaccharides such as gum arabic, alginic acid and salts thereof, CMC (carboxymethyl cellulose) and xanthan gum, inorganic substances such as aluminum magnesium silicate and alumina sol, antiseptics, coloring agents, and stabilizers such as PAP (isopropyl acid phosphate) and BHT.

In the present method, for example, Compound (1) and Compound (A) may be separately made into formulations by the method described above and the like and further diluted with water as needed, and a mixture obtained by mixing the formulations or dilutions can be used.

In the present method, another one or more fungicides or insecticides can be mixed and applied. As the fungicides and insecticides, known ones can be used.

Specifically, the methods for treating crops in the present method include a treatment to crop foliage such as foliage application, a treatment to crop cultivation areas such as soil treatment, a treatment to crop seeds such as seed disinfection, and the like.

Examples of the treatments to crop foliage in the present method include treatment methods in which a formulation is applied to crop surfaces, such as foliage application and trunk application. As treatment methods in which a crop before planting out is allowed to directly absorb a formulation, a method of immersing the whole crop or the root part is mentioned. A formulation obtained by using a solid carrier such as mineral powders can be attached to the root part.

Examples of treatments to crop cultivation areas in the present method include application to soils, soil incorporation and soil drenching with chemicals (irrigation of chemical liquids, soil injection, dripping of chemical liquids), and examples of places to be treated include planting holes, furrows, around planting holes, around furrows, the whole surface of cultivation areas, parts adjacent to soils in plants, the spaces between roots, under trunks, ridges between trunks, ridging, seedling boxes, seedling trays, seedbeds and the like, and times to be treated include before sowing, at the time of sowing, immediately after sowing, in the seedling stage, before planting, at the time of planting, in the growing stage after planting (the initial flowering stage, the full flowering stage, the final flowering stage and the reproductive stage) and the like. In the treatments to crop cultivation areas, crops and soils can be simultaneously treated with active components, and a solid fertilizer such as a paste fertilizer containing active components can be also applied to soils. Active components can be mixed with irrigation liquids, and examples thereof include injection into irrigation equipment (irrigation tube, irrigation pipe, sprinkler etc.), mixing into a flooding liquid between furrows, mixing into hydroponic water and the like. An irrigation liquid and active component can be mixed in advance to be used for the treatment using proper irrigation methods such as the irrigation methods mentioned above and other methods such as water spray and flooding, for example.

The treatments to crop seeds in the present method are, for example, a method for treating crop seeds, bulbs and the like with the present composition, and examples thereof include spray treatments in which a suspension of Compound (1) and Compound (A) is sprayed in the form of mist on seed surfaces or bulb surfaces, smear treatments in which, for example, a wettable powder, an emulsifiable concentrate or a flowable of Compound (1) and Compound (A) is applied to seeds or bulbs after adding a small amount of water or directly, and immersion treatments in which seeds are immersed in a solution of Compound (1) and Compound (A) for a certain period of time, film coating treatments, and pellet coating treatments.

The amounts of Compound (1) and Compound (A) applied vary depending on the kind of crop to be treated, the kind of plant disease to be prevented and the occurrence frequency thereof, formulation forms, application time, application methods, places to be applied, weather conditions and the like, and, when treating crop foliage or when treating cultivation areas, the total amount of Compound (1) and Compound (A) (hereinafter, referred to as "the amount of active components") is usually 1 to 500 g, preferably 2 to 200 g and more preferably 10 to 100 g per 1000 $m^2$. In the treatments to seeds, the amount of active components is usually 0.001 to 10 g and preferably 0.01 to 1 g per kilogram of seeds.

Emulsifiable concentrates, wettable powders, suspending agents and the like are usually diluted with water and sprayed. In this case, the concentration of the amount of active components is usually 0.0005 to 2% by weight and preferably 0.005 to 1% by weight. Dusts, granules and the like are usually treated without dilution.

The present method is applied to the "crops" mentioned below.

Farm products such as corn, rice, wheat, barley, rye, oat, sorghum, cotton, soybean, adzuki bean, kidney bean, peanut, sarrazin, sugar beet, rapeseed, sunflower, sugar cane and tobacco;

vegetables such as Solanaceae vegetables (eggplant, tomato, green pepper, hot pepper, potato etc.), Cucurbitaceae vegetables (cucumber, pumpkin, zucchini, watermelon, melon, squash etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus), Umbelliferae vegetables (carrot, parsley, celery, parsnip etc.), Chenopodiaceae vegetables (spinach, Swiss chard etc.), Labiatae vegetables (Japanese mint, mint, basil etc.), strawberry, sweet potato, yam and aroid;

fruit trees such as pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruits etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date and coconut; and trees other than fruit trees such as tea and mulberry.

The "crops" also include transgenic plants.

Among the "crops", rapeseed, rice, corn, wheat, barley, kidney bean, soybean, peach, apple, common pear or the like is mentioned as a preferred crop.

According to the present invention, seeds or fruits of a crop can be increased in number or weight.

EXAMPLES

The present invention will now be described in more detail byway of formulation examples and a test example thereof. It should be noted, however, that the present invention is not limited only to the following examples. Unless otherwise specified, in the following examples, parts indicate parts by weight.

Formulation Example 1

Five parts of Compound (1), 5 parts of Compound (A), 35 parts of a mixture of white carbon and polyoxyethylene alkyl ether sulfate ammonium salt (weight ratio 1:1) and 5 parts of water are mixed and the obtained mixture is pulverized by a wet grinding method to obtain each flowable formulation.

Formulation Example 2

Ten parts of Compound (1), 5 parts of Compound (A), 1.5 parts of sorbitan trioleate and 28 parts of aqueous solution containing 2 parts of polyvinyl alcohol are mixed and the obtained mixture is pulverized by a wet grinding method, and 45.50 parts of aqueous solution containing 0.05 parts of xanthan gum and 0.1 parts of aluminum magnesium silicate are then added thereto. Further, 10 parts of propylene glycol are added thereto and the obtained mixture is stirred and mixed to obtain a flowable formulation.

Formulation Example 3

Ten parts of Compound (1), 40 parts of Compound (A), 3 parts of calcium lignin sulfonate, 2 parts of sodium lauryl sulfate, and 45 parts of synthetic hydrated silicon dioxide are well ground and mixed to obtain each wettable powder.

Test Example 1

Seeds of rapeseed were sown at a density of 3.5 kg/hectare on Sep. 3, 2010 and raised. A 25% flowable formulation of Compound (1) and tebuconazole (: Horizon (registered trademark) 25% EW) were diluted with water. These were mixed to prepare a composition so that Compound (1) and tebuconazole might be each 150 g/hectare. The foliage of rapeseed in the full flowering stage (growth stage BBCH 65 (Biologische Bundesanstalt Bundessortenamt and Chemical industry (BBCH-scale))) was treated with the composition on May 19, 2011. The amount treated was 200 L/hectare. The test area was 3×8 m, and a test zone treated with the chemical by the operation mentioned above was referred to as a treated zone. Meanwhile, a test zone with the same test area which was not treated with the chemical was referred to as a non-treated zone. Seeds of the rapeseed were harvested on Aug. 9, 2011, and the yield per hectare was investigated. The water content of the rapeseed seeds as the target of the investigation was considered to be 9%. As a result, a yield of 4.3 ton/hectare was obtained in the treated zone, while in the non-treated zone, the yield was 3.8 ton/hectare. During the test period, the occurrence of insect pests which can affect yields was not observed.

Yields of crop seeds can be increased by mixing and using Compound (1) and Compound (A) at a weight ratio of 3:4 and carrying out the same operation as in Test Example 1.

The invention claimed is:
1. A method for increasing the number or weight of seeds or fruits of a crop, the method comprising a step of:
treating the crop with a formulation consisting of a compound represented by Formula (1)

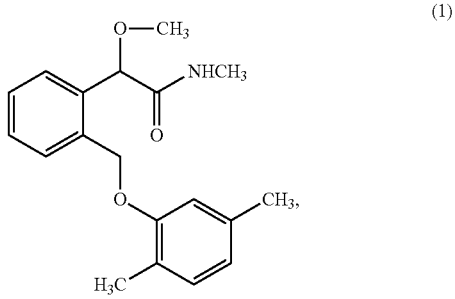 [SMILES: CNC(=O)C(OC)c1ccccc1COc1cc(C)ccc1C]

tebuconazole, and an inert carrier, wherein the compound of Formula (1) and tebuconazole are administered in effective amounts to increase the number or weight of seeds and fruits of the crop.

2. The method according to claim 1, wherein the weight ratio of the compound represented by Formula (1) to tebuconazole is 0.0125/1 to 500/1.

3. The method according to claim 1, wherein the compound represented by Formula (1) has an R absolute configuration.

4. The method according to claim 1, wherein the crop is rapeseed, rice, corn, wheat, barley, kidney bean, soybean, peach, apple or common pear.

* * * * *